United States Patent [19]

Aihara

[11] 4,406,547
[45] Sep. 27, 1983

[54] APPARATUS FOR EFFECTING AUTOMATIC ANALYSIS

[75] Inventor: Takayuki Aihara, Hachioji, Japan

[73] Assignee: Olympus Optical Company Limited, Tokyo, Japan

[21] Appl. No.: 175,440

[22] Filed: Aug. 6, 1980

[30] Foreign Application Priority Data

Aug. 7, 1979 [JP] Japan ................................ 54-99841
Aug. 7, 1979 [JP] Japan ................................ 54-99842
Aug. 7, 1979 [JP] Japan ................................ 54-99843

[51] Int. Cl.³ .......................................... G01N 21/25
[52] U.S. Cl. .................................. 356/414; 356/418; 422/64
[58] Field of Search ............... 356/409, 411, 414, 418, 356/419, 427; 422/64

[56] References Cited

U.S. PATENT DOCUMENTS 3,609,047 9/1971 Marlow .............................. 356/419
3,882,318 5/1975 Mioduski ........................... 356/414
4,061,428 12/1977 Amano et al. ..................... 356/418
4,305,723 12/1981 Kolber et al. ...................... 422/64

Primary Examiner—Bruce Y. Arnold
Attorney, Agent, or Firm—Parkhurst & Oliff

[57] ABSTRACT

An automatic chemical analyzer comprising a turntable is disclosed which holds a number of cuvettes containing test liquids to be analyzed and is rotated about a center axis step by step at a given repetition rate, a panchromatic light source is arranged to project radially a measuring light beam from the center axis to the cuvettes, and a light detector is arranged in the center axis to receive the measuring light beam transmitted through the test liquid via prisms. A rotating filter holder is arranged in front of the light detector to insert given filter elements into the measuring light beam path so as to effect colorimetric measurement with desired wavelengths.

21 Claims, 18 Drawing Figures

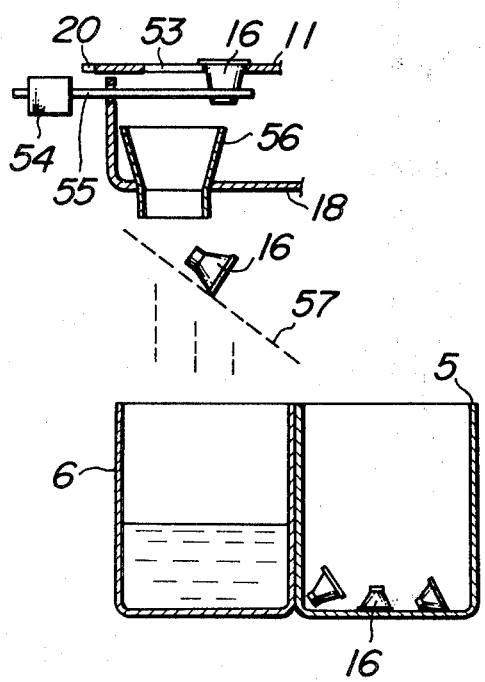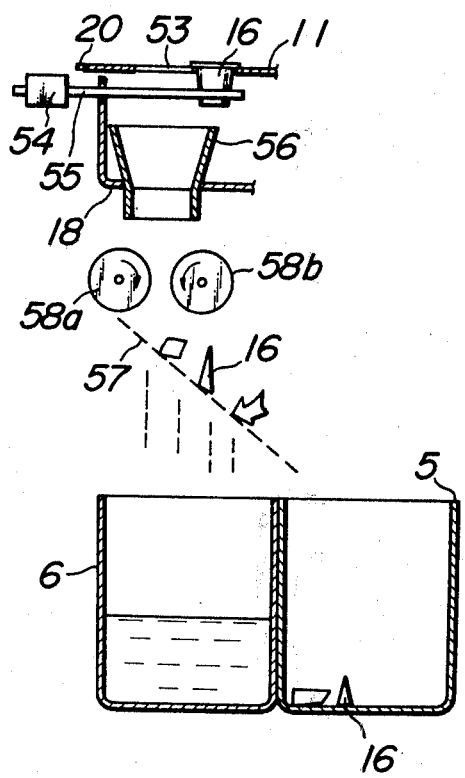

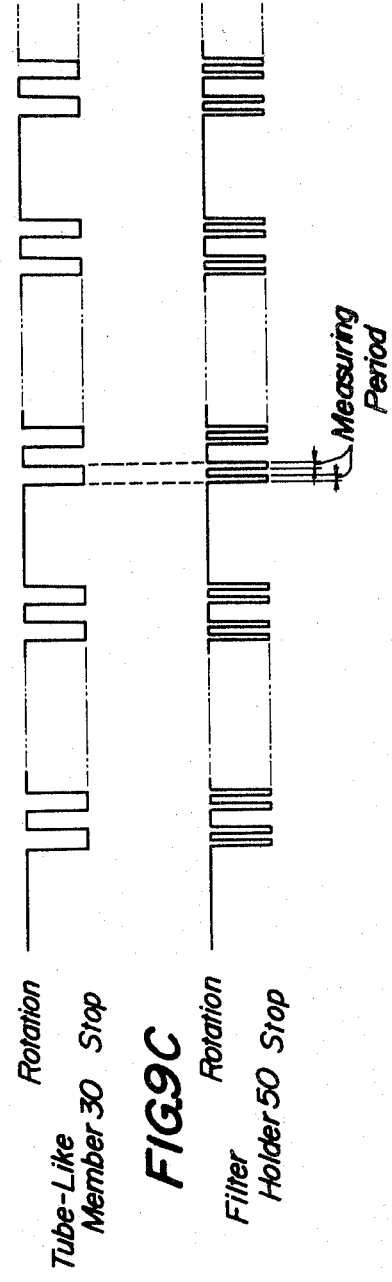

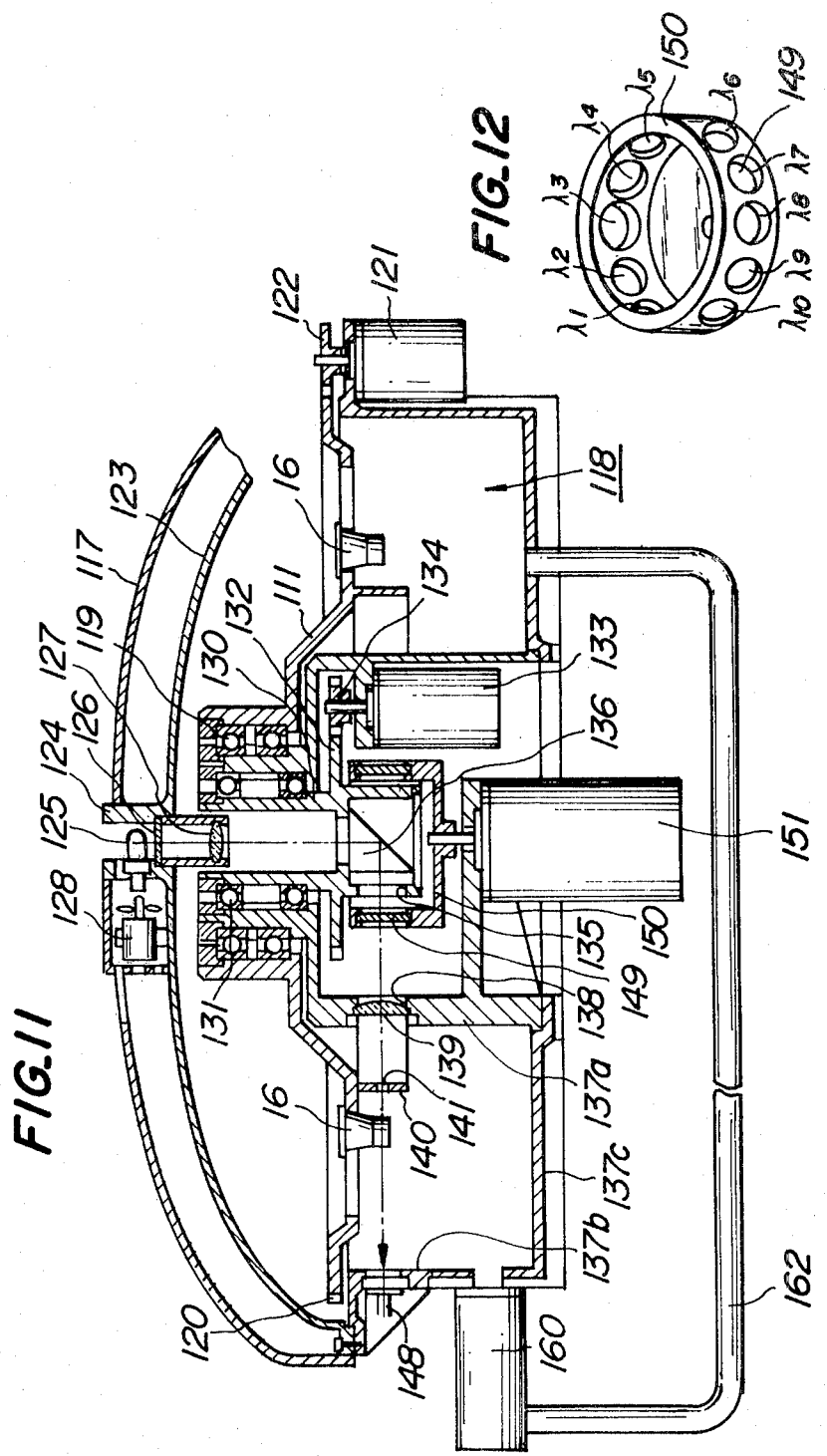

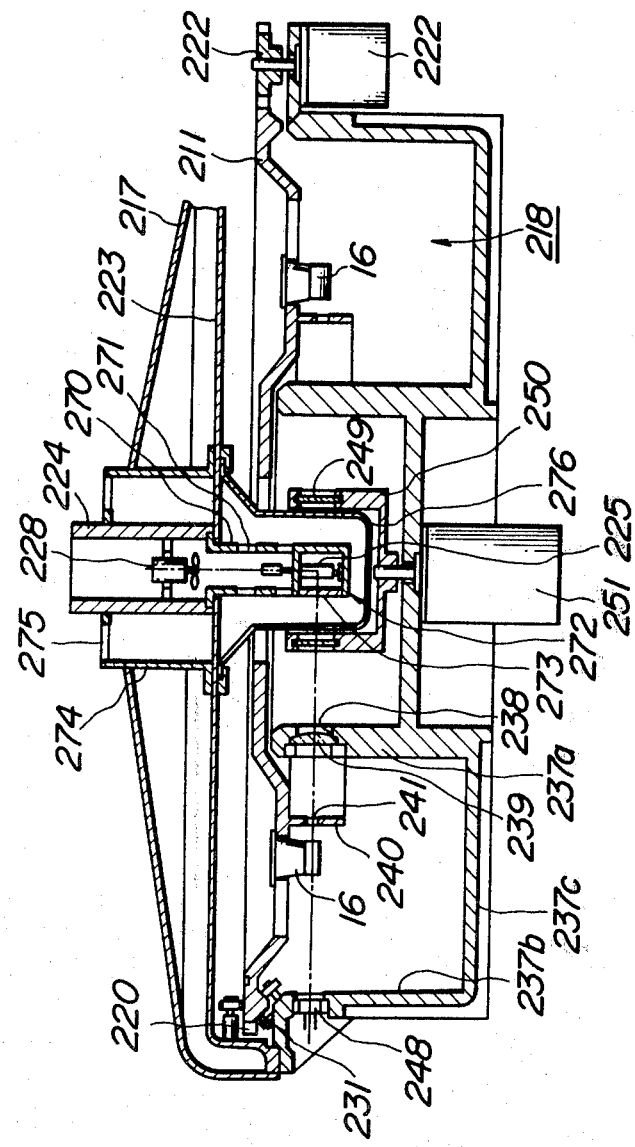

APPARATUS FOR EFFECTING AUTOMATIC ANALYSIS

BACKGROUND OF THE INVENTION

This invention relates to an automatic analyzing apparatus for automatically effecting chemical analyses for various sample fluids such as (but not limited to): cerebrospinal fluid, blood, urine, and the like.

Automatic chemistry analyzers can be roughly divided into two broad categories: continuous flow or discrete systems. Presently the majority of analyzer models employ the discrete approach to automation.

In a discrete system, each test is carried through the analytical process in its own discrete container or compartment. Current discrete analyzers can be further classified into two major sub-categories; sequential and centrifugal analyzers.

In sequential testers, all tests are performed sequentially, one after another, so that at any given point in time all tests in process are in a somewhat different stage of progress. In general, sample and reagent are metered into a vessel which is fed along a given path and the test liquids in each of the vessels are treated to each aspect of the analysis (reagent addition, mixing, quantitating, etc.) in sequence.

Centrifugal analyzers are also discrete, but test liquids are processed in parallel to one another. All samples in process are in the same stage of analysis at the same time. In operation, samples and reagent are pre-measured and pre-loaded into appropriate compartments arranged about the circumference of a rotor disc, whereupon it is placed on a centrifuge and rotated at a high speed past a photometer device. Centrifugal force mixes all samples with reagent at the same time and hence each of the test liquids is in the same stage of analysis at any given point in time.

The majority of analyzers, regardless of the above mentioned categories, are capable of performing more than one type of test item. There are three broad categories of methods for providing multi-test capability.

What shall hereinafter be referred to as Random Access Testers currently require individual test packs which are pre-packaged with the appropriate reagents required to perform one test of a given test type. These test packs are loaded into the intrument system according to the analyst's needs, charged with a sample liquid, and processed in a discrete manner. Random access testers offer great convenience and flexibility but currently available embodiments have low productivities when compared with other means of providing multi-test item capability. In addition, the requirement for pre-packaged test packs makes operating costs much higher than the alternate methods.

Another means of performing a plurality of tests on each of a plurality of samples is sequentially by test-item batch. All samples are analyzed sequentially or centrifugally for a given test item. When all samples have been analyzed for a give test item, the system is changed over, or somehow modified, to perform a different test item and all appropriate sample are re-treated. When all samples have been processed for the required test items, the results of each sample's test items must be collated to allow including all of a given samples analytical results on a single report form for return to a physician, etc. Such systems are usually referred to as 'single channel' systems. Single channel systems are usually considered most appropriate for treating a batch or plurality of samples, as the effort required to change-over from one test item to another is generally neither convenient nor cost-effective to treat one sample for a plurality of test items. Additionally, at any given moment in time, only one test item is available for immediate use.

Simultaneous analyzers have a plurality of analytical channels which enable a plurality of test items to be performed simultaneously on each sample. Such systems are commonly referred to an 'multi channel' analyzers. Multi-channel analyzers do make more than one test item available at any given point in time, do eliminate the data collating task required of single channel analyzers and in general, do have higher productivities than single-channel analyzers by virtue of the fact that they are constructed as a plurality of single-channel analyzers combined into one device. This last feature is a drawback in that it makes the analyzer system complicated in construction, large in size, and generally, much higher in cost than single-channel discrete, continuous flow or centrifugal analyzers.

In the known analytical systems of the noncentrifugal type, photometric quantitation is carried out after some time period from the initiation of the test reaction, i.e. when the test liquid has traveled along the processing line by some given fixed distance. Therefore, the reaction time is fixed as a function of the length or circumference of the processing line, which may or may not be optimal with respect to a given test item and/or sample.

Additionally, sequential testers have only one photometer position per channel, severely limiting the amount of photometric data which can be made available. No photometric data can be made available until a test liquid reaches the photometer station, typically, 8–10 (often 30) minutes from the time of mixing of sample with reagent. Once a test liquid reaches a photometer station, the amount of time which is devoted to photometric measurement essentially limits the speed of analysis of a given sequential tester, i.e. if 60 seconds is devoted to photometric quantitation, then the processing rate is limited to 60 tests per hour. This feature forces a trade-off between processing rate and photometric quantitation time especially for 'kinetic' test (ex. enzyme rate tests) which require photometric measurement over long periods of time in order to provide for best accuracy and precision of analysis.

In order to overcome such disadvantages the applicant has developed a new automatic chemical analyzer in which reaction states of test liquids are monitored in a reaction line and given quantitative measurements are effected after the test liquids have been certified that they have reached given desired reaction condition. Such an analyzer has been disclosed in U.S. patent application Nos. 139,469 and 139,470 (now U.S. Pat. No. 4,338,279, ) both filed on Apr. 11, 1980. According to such an analyzer, since the analytical datum for respective test liquids can be obtained always under given desired reaction conditions, highly reliable analytical results can be achieved. In the automatic chemical analyzer disclosed in the U.S. patent application Ser. No. 139,470, a monitoring photometric section is provided in the reaction line for monitoring the reaction condition. When the test liquid has been detected to reach the desired reaction condition, the test liquid is transferred to a precise measuring section provided out of the reaction line and the precise measurement is effected at this precise measuring section. Therefore, there must be provied two sets of measuring sections and a mechanism for transferring the test liquids from the monitoring section to the precise measuring section. Thus, the whole apparatus is liable to be complicated and large. Further in the analyzer disclosed in the U.S. patent application Ser. No. 139,469, a single light source is arranged at a rotational center axis of a turn-table holding a plurality of cuvettes, a cylindrical body having one or more slits formed therein is rotated about the light source to project a measuring light beam through the slits onto successive cuvettes, and the light flux transmitted through the cuvettes is made incident upon a light detector by means of a number of optical fiber bundles. Since the optical fibers are arranged at respective cuvettes, a cuvette feed path is covered with the optical fiber bundles. In case of feeding the cuvettes in an air bath, an air stream could not flow smoothly due to the fiber bundles and thus, a temperature variation might be produced to effect a measuring accuracy. Further since the optical fiber bundles are expensive, the cost of the whole apparatus is liable to be high. Moreover, the optical fibers have lower transmittivity in the ultraviolet ray range, so that the analytical accuracy might be deteriorated. If a light source of high power is used in order to increase the measuring accuracy, the apparatus is liable to become large in size.

SUMMARY OF THE INVENTION

The present invention has for its object to provide a novel and useful automatic chemical analyzing apparatus which can obviate the above mentioned various drawbacks and can produce analytical data of high reliability with a simple construction.

An automatic chemical analyzing apparatus according to the invention comprises a cuvette turntable for supporting a number of cuvettes along a circle and arranged rotatably about a center axis of the circle;

means for rotating intermittently the cuvette turntable about said center axis at a give repetition rate;

a light source fixedly arranged to project a measuring light beam along the center axis;

a first optical member rotatably arranged about said center axis for deflecting radially with respect to the cuvette turn table, the measuring light beam toward the cuvette held in the cuvette turn table;

a plurality of second optical members arranged at a plurality of positions outside the cuvette travelling circle for receiving the measuring light beam transmitted through the cuvettes and deflecting the light beam toward the center axis;

a third optical member arranged at the center axis integrally with the first optical member for deflecting the measuring light beam into the center axis;

a single light detector arranged on the center axis to receive the light beam deflected by the third optical member; and means for rotating the first and third optical members about the center axis at a higher rate than that of the cuvette turn table; whereby while the cuvette turn table is stopped, the cuvettes situated at the positionns corresponding to the second optical members are successively scanned by rotating the first and third optical members.

BRIEF DESCRIPTION OF THE DRAWINGS

FIGS. 8A and 8B are cross sections illustrating two embodiments of a mechanism for discharging cuvettes and test liquids separately from each other;

FIGS. 9A, 9B and 9C are timing charts for explaining the operation of the measuring section;

FIG. 11 is a cross section illustrating another embodiment of the measuring section according to the invention;

FIG. 12 is a perspective view showing a filter holder of the apparatus of FIG. 11; and FIG. 13 is a cross section illustrating still another embodiment of the measuring section according to the invention.

DESCRIPTION OF THE PREFERRED EMBODIMENTS

Figure 1:
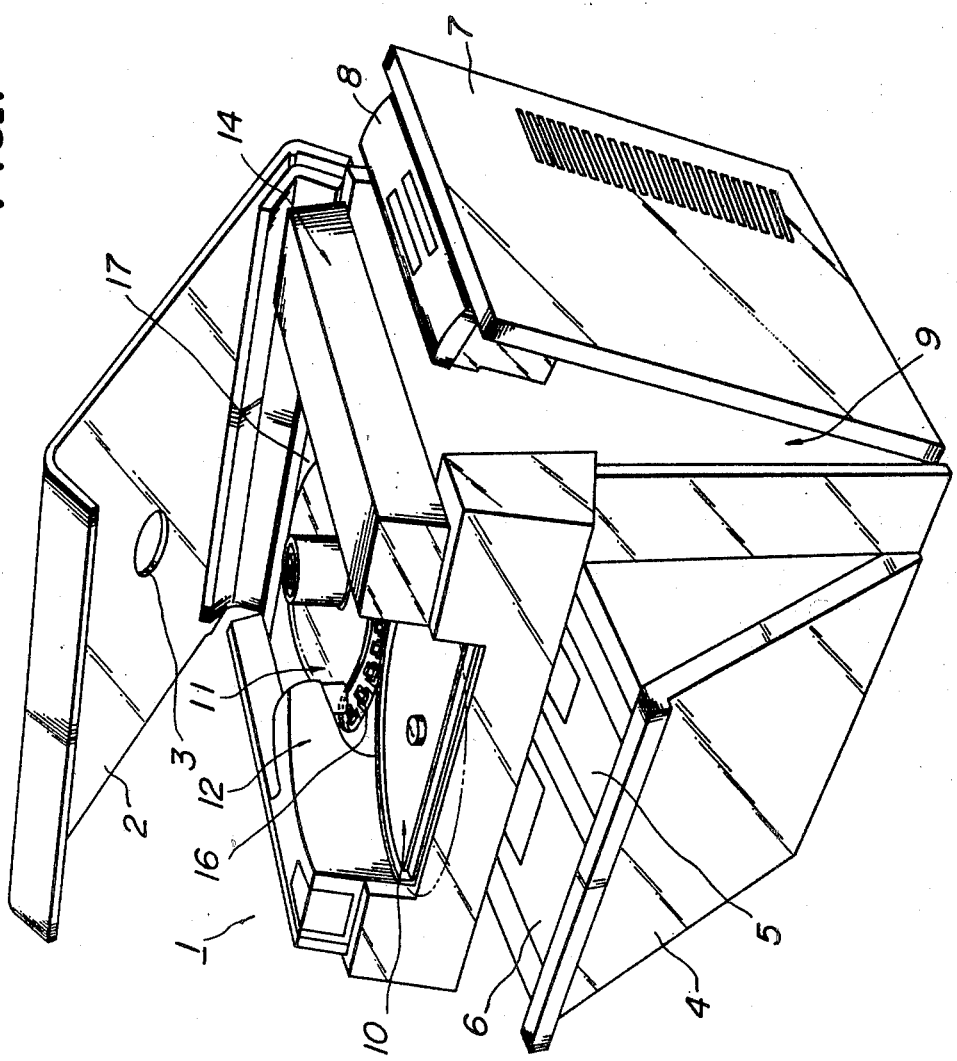
FIG. 1 is a perspective view illustrating an embodiment of the automatic analyzing apparatus according to the invention.
Figure 2:
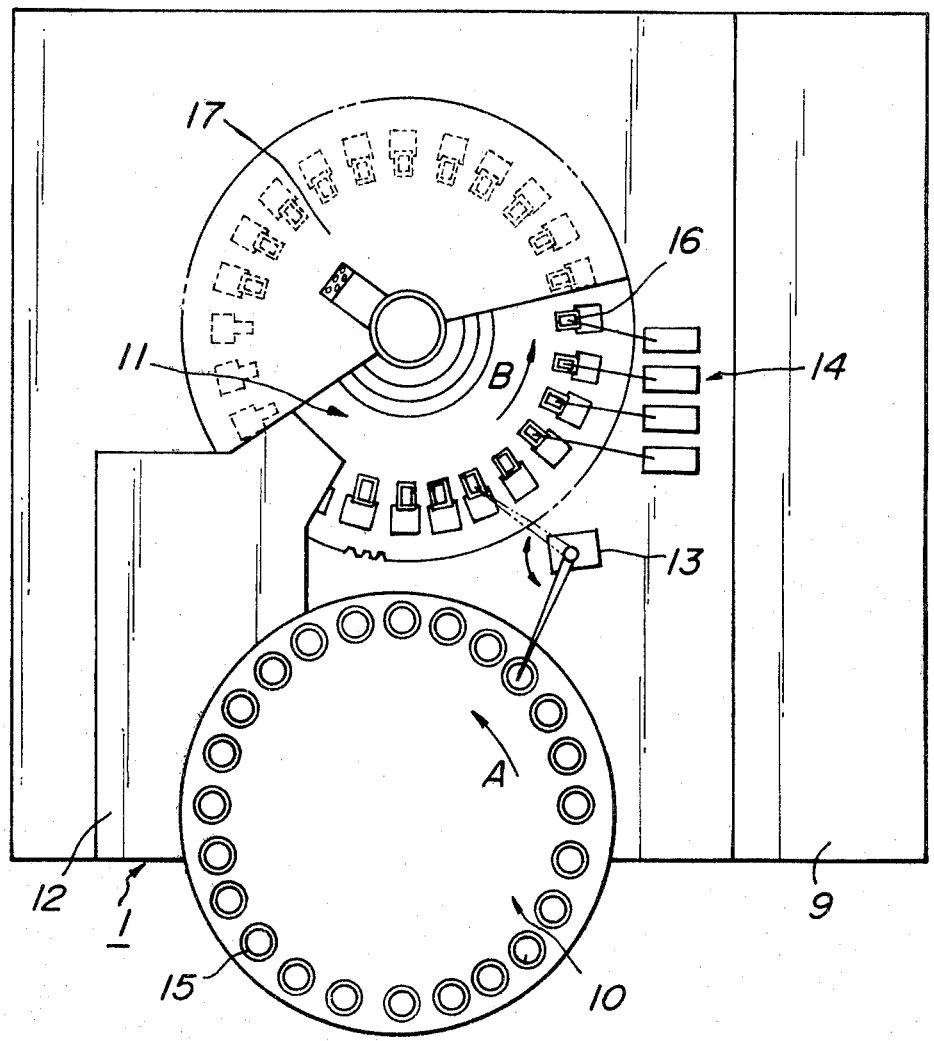
FIG. 2 is a plan view showing schematically the apparatus of FIG. 1.

FIGS. 1 and 2 are perspective and plan view illustrating an outer appearance of an embodiment of the automatic analyzing apparatus according to the invention. A main body 1 includes a cover 2 hinged at the rear to provide access to internal components. In the cover 2 is formed on opening 3 for dissipating heat produced by light source of the colorimetrically measuring section to be described later. A front plate 4 is secured to the main body 1 in such a manner that the front plate can be opened to provide access. A cuvette container 5 for storing waste cuvettes and a waste liquid container 6 for storing waste liquid are detachably secured to the front plate 4. A right-hand side plate 7 is hinged to the main body 1 at the bottom side, and a cassette holder 8 for supporting a detachable reagent cassette for holding various reagent bottles necessary for given analyses is provided on the side plate 7. A portion for fitting the cassette holder 8 defined by the right-hand side plate 7 forms a refrigerator 9.

A sample-liquid feed mechanism 10, a cuvette feed mechanism, i.e a cuvette turn table 11, and a cuvette supply mechanism 12 are provided on the main body 1 at its front portion, back portion and left-hand portion, respectively. At the right-hand portion of the main body 1 are provided a sample delivery mechanism 13, and a reagent delivery mechanism 14. In this embodiment, the reagent delivery mechanism 14 comprises four reagent delivering pumps connected to different diluents and/or buffer solutions.

The sample liquid feed mechanism 10 and cuvette feed mechanism 11 comprise disc-shaped rotating members, (i.e. turn tables) which can rotate intermittently in a horizontal plane in directions shown by arrows A and B, respectively and hold detachable sample vessels 15 and cuvettes 16, respectively, about their peripheries.

As illustrated in FIGS. 1 and 2, a cover 17 is provided for covering the cuvette travelling line, i.e. the reaction line of the cuvette feed mechanism 11 from the reagent delivery section to the cuvette supply section. Underneath the cover 17 is arranged the measuring section which comprises a monitoring and measuring photometer. After the measurement the cuvette 16 falls down from the turntable 11 and the cuvette and test liquid are separately disposed in the waste cuvette container 5 and waste liquid container 6, respectively by means of a cuvette-liquid separating means which will be described later.

Figure 3:
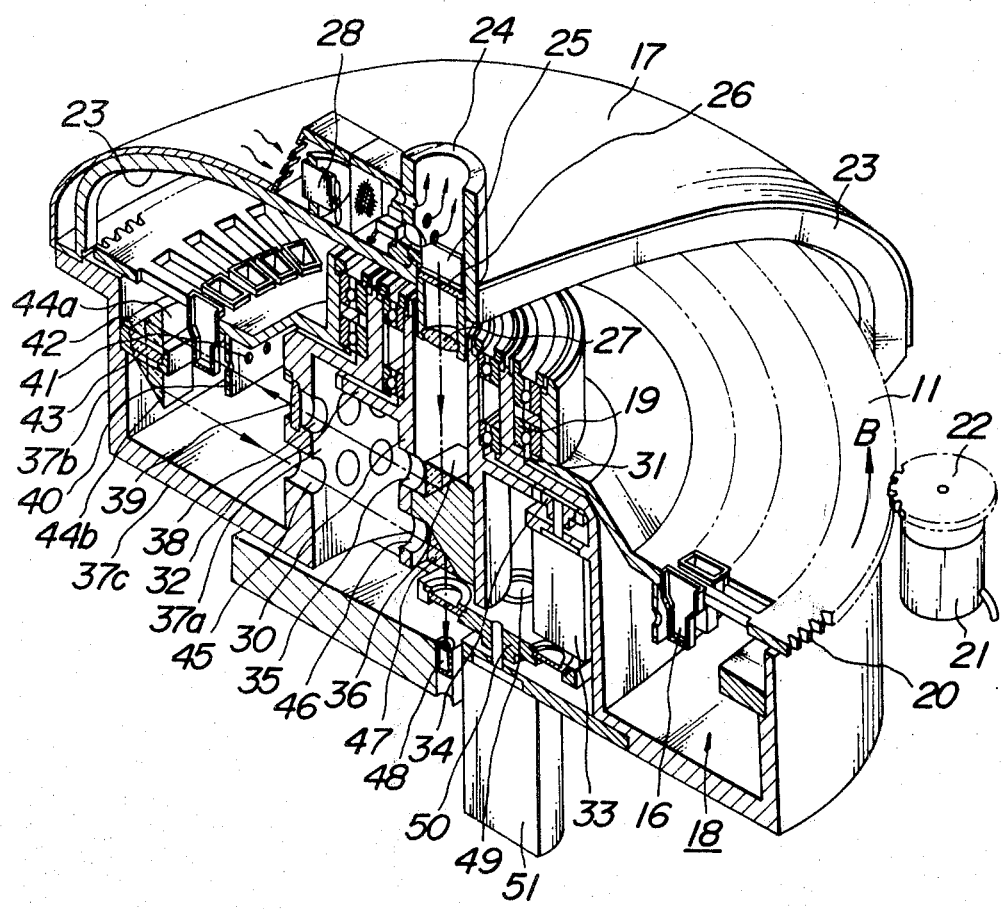
FIG. 3 is a cross section showing in detail an embodiment of a measuring section of the automatic analyzing apparatus of FIG. 1.

FIG. 3 is a cross section showing the measuring section taken along a diameter of the cuvette turn table 11. The turntable 11 is supported rotatably on a thermostat 18 constituting an air bath by means of a bearing 19. The thermostat 18 is formed by an inner wall 37a, an outer wall 37b and a bottom wall 37c. The circumference of the turntable 11 is provided with a gear 20 which is engaged with a gear 22 connected to a driving shaft of electric motor 21. The motor 21 is so energized that the table 11 is rotated intermittently in the direction B at a given constant rate. At a rotating center axis of the turn table 11 is arranged a cylinder 24 which is connected to the outer wall 37b of the thermostat 18 by means of bridge members 23. The cover 17 is placed on the bridge members 23. In the cylinder 24 is arranged a panchromatic light source (white light source) 25 aligned with the rotating center axis. Below the light source 25 are provided a heat absorbing glass plate 26 and a lens 27 which downwardly projects a parallel light beam along the rotating center axis. On the bridge 23 is secured a fan 28 for cooling the light source 25.

Below the cylinder 24 a tube-like member 30 is provided which is rotatably connected to the thermostat 18 by means of a bearing 31. A gear 32 is secured on an outer surface of the tube-like member 30. The gear 32 is engaged with a gear 34 coupled to an output shaft of an electric motor 33 which is fixed to the thermostat 18. In this manner the tube-like member 30 can be rotated by energizing the motor 33. In the tube-like member 30 is arranged a first optical member formed by a prism which projects the parallel light beam from the lens 27 through a slit hole 35 formed in the tube-like member 30 onto the cuvette 16 held on the cuvette turn table 11.

In the inner wall 37a of the thermostat 18 are formed a number of slit holes 38 through which the measuring light beam is selectively projected onto the cuvettes 16. In these slit holes 38 are secured lenses 39. Integrally with the turntable 11 is formed a light shielding flange 40 which projects into the thermostat 18. In the shielding flange 40 are formed a number of slit holes 41 corresponding to the respective cuvettes 16 for introducing the light beam into the cuvettes.

Between each cuvette 16 and the outer wall 37b of the thermostat 18 is arranged a second optical member 42 comprising a lens 43 and two prisms 44a and 44b. These are arranged so that the light beam transmitted through the cuvette 16 is deflected toward the rotating center axis of the turn table 11. In the inner wall 37b of the thermostat 18 and the tube-like member 30 are formed slit holes 45 and a hole 46, respectively for passing the deflected light beam.

Figure 4:
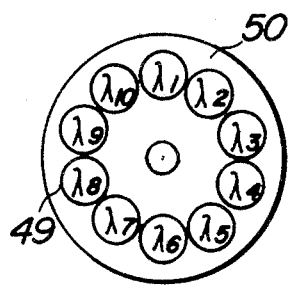
FIG. 4 is a plan view illustrating an embodiment of a filter holder.

In the tube-like member 30 is arranged a third optical member 47 including of a prism for deflecting the transmitted light beam through the cuvette 16 along the rotating center axis in a downward direction. Underneath the third optical member 47 is arranged a single common light detector 48 aligned with the rotating center axis so as to receive the light beam reflected by the prism 47. Between the third optical member 47 and the light detector 48 is arranged a rotating filter holder 50 holding along its periphery a plurality of filter elements 49 having different transmitting wavelengths $\lambda_1$–$\lambda_{10}$ as shown in FIG. 4. The filter holder 50 is secured to the output shaft of an electric motor 51 fixed to the thermostat 18. Therefore, by energizing the motor 51 in a suitable manner, any desired one of filter elements 49 can be selectively inserted into the light beam path between the third optical member 47 and the light detector 48. Output signals from the light detector 48 are supplied to a processor through an analog-digital converter (not shown) and can be treated in the processor.

Figure 5:
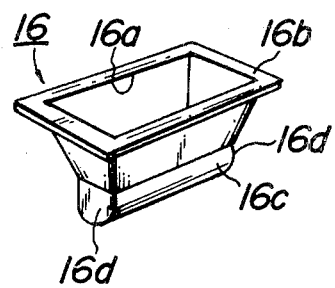
FIG. 5 is a perspective view showing an embodiment of a cuvette for use in the apparatus according to the invention.

FIG. 5 is a perspective view illustrating an embodiment of the cuvette 16. The cuvette 16 of this embodiment comprises a rectangular opening 16a and a supporting flange 16b provided at the periphery of the opening. The opening is connected to a bottom portion 16c by a tapered side wall narrowing towards the bottom portion. The bottom portion 16c is formed as a semi-cylindrical shape and has measuring windows 16d at both ends, when viewed in its axial direction, through which windows the test liquid in the cuvette is optically measured.

Figure 6A:
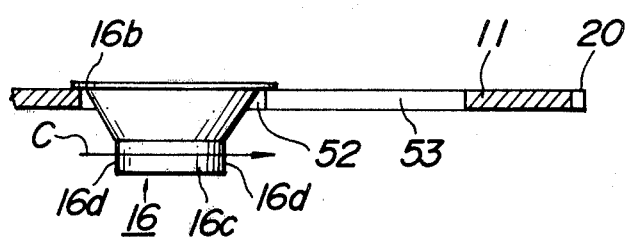
FIGS. 6A and 6B are partially cross sectional views illustrating a manner of holding and discharging the cuvette.
Figure 6B:
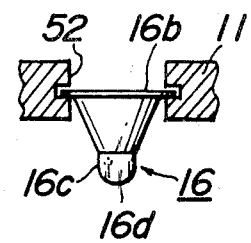

According to the above mentioned construction of the cuvette 16, since the opening 16a (receiving port) is wide, it is possible to easily deliver the sample and reagent without splashing. Further, the amount of test liquid is sufficient to fill the semi-cylindrical bottom portion 16c, and thus the analysis can be effected with very small amounts of sample and reagent. Moreover, since the measurement axis extends in a longitudinal direction of the cuvette and thus, is sufficiently long, it is possible to carry out the analysis with very high sensitivity. Since the side wall is tapered from the opening 16a to the bottom 16c, and the flange 16b is provided around the opening, the cuvette may be simply secured to the cuvette turn table 11. That is, the flange 16b may be placed on a holding member 52 as illustrated in FIG. 6A, or may be detachably inserted into recesses formed in a holding member 52 as depicted in FIG. 6B.

In this manner, the cuvette 16 may be simply supported by the holding member without making the measuring windows 16d contact the holding member 52, and thus the measuring windows can be protected against injury. In FIG. 6A, an arrow C denotes the optical measuring axis. Further, the cuvette 16 may be formed by molding a transparent material, and thus its mechanical strength can be made high.

Figure 7:
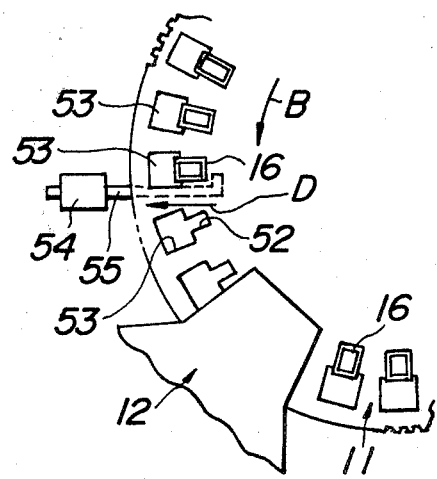
FIG. 7 is a plan view showing an embodiment of a mechanism for removing cuvettes from a cuvette turn table.

FIG. 7 is a plan view of an embodiment of a mechanism for removing the cuvette 16 from the turn table 11. The removing mechanism is arranged at an upstream position with respect to the cuvette supply mechanism 12 viewed in the rotating direction B. In this embodiment, the cuvette 16 is held by the turntable 11 with its flange 16b being placed on the table 11 at the holding opening 52 as illustrated in FIG. 6A or with its flange 16b being inserted into the recesses formed in the holding opening 52 as shown in FIG. 6B. In order to drop the cuvette 16 off the turntable 11, a discharging opening 53 is formed in the turntable 11 integrally with the supporting opening 52, said discharging opening 53 having a dimension sufficiently larger than the cuvette 16. At the discharging station is arranged an L-shaped arm 55 movable in the radial direction of the turn table 11 and an outer end of the arm 55 is connected to a plunger of a solenoid 54. When the solenoid 54 is energized, the arm 55 is moved in a direction D so as to pull the cuvette 16 into the opening 53. Then the cuvette 16 falls down from the turntable 11 through the opening 53.

Next, a mechanism for disposing of the cuvettes and test liquids after photometric measurement will be described. In this embodiment, waste liquids are not directly discharged from the analyzing apparatus. In the apparatus is provided a mechanism for separately disposing waste liquids from the cuvettes into the waste cuvette container 5 and waste liquid container 6, respectively.

FIG. 8A is a cross section showing an embodiment of such a disposal mechanism. The cuvette 16 is held by the supporting mechanism at each photometric position of the photometric measurement section. After measurement, the supporting mechanism shown in FIG. 7 is driven and the cuvette 16 is allowed to fall. Underneath the cuvette 16 is a hopper 56 for guiding the falling cuvette 16 and below the hopper an inclined mesh 57. The falling cuvette 16 strikes the mesh 57 and the contents of the cuvette spilled into the container 6. The cuvette 16 slides downward on the mesh 57 until it is allowed to fall into the cuvette waste tank 5.

FIG. 8B illustrates another embodiment of the disposing mechanism. In this embodiment a pair of rollers 58a and 58b are arranged between the hopper 56 and the mesh 57. The falling cuvette 16 is inserted between the rollers and is broken into fragments. In this manner the cuvette 16 and the test liquid can be positively separated from each other.

Now the operation of the above mentioned analyzing apparatus will be explained.

At first sample liquids are supplied into the sample cuvettes 15 and the cuvettes are set in the intermittently rotating sample feed mechanism 10. In the cuvette turntable 11, which rotates intermittently in the direction B, are supplied successively the empty cuvettes 16 from the cuvette loading mechanism 12. In the cuvette 16 set in the turntable 11 are supplied, at a given position, sample liquid and diluent from the sample delivery mechanism 13. After the cuvette 16 has advanced by several steps, desired reagent, diluent and/or buffer solution are supplied from the reagent delivery pump connected to the diluent and/or buffer solution tank. At the same time the liquids contained in the vessel 16 are mixed to form a test liquid.

The tube-like member 30 is rotated at a speed higher than the cuvette turn table 11 and, during this rotation, the measuring light beam is projected onto a plurality of the second optical members 42 arranged at given positions. Therefore, each cuvette 16 arrives at the corresponding measuring positions opposed to the second optical members 42 and the test liquid contained therein is subjected to photometric tests several times during the rotation of the turn table 11. While the cuvette 16 is situated at the respective measuring positions, the filter holder 50 is turned to introduce one or more desired filter elements 49 in the optical path. If a plurality of filter elements are selected, the measurements with a plurality of wavelengths can be effected.

Now the operation will be further explained with reference to numerical examples. The cuvette turntable 11 rotates by one step during a period of six seconds, and the respective cuvettes 16 are to be measured every 24 seconds. The cuvette turntable 11 may hold a hundred cuvettes 16 along its circumference. However, in practice, for several cuvettes situating from the cuvette discharging position to the reagent delivery position it is impossible to carry out the measurement because, in this region, the test liquid is not in the cuvette. For instance, if fifteen cuvettes among a hundred cuvettes on the table 11 are positioned in said range it is sufficient to measure the remaining eighty five cuvettes at such a rate that for each cuvette the colorimetric measurement is effected every twenty four seconds. To this end twenty-two second optical members 42 are arranged every four steps of the turn table 11. While the turntable 11 is stopped, twenty-two cuvettes situated at the twenty-two measuring positions corresponding to the twenty-two optical members 42 can be successively scanned by rotating the tube-like member 30 intermittently. While the tube-like member 30 is stopped, the filter holder 50 is rotated intermittently so as to insert one or more given filter elements 49 in the measuring light path.

FIG. 9 is a time chart for showing the mutual relation of the cuvette turntable 11, the tube-like member 30 and the filter holder 50. In this embodiment, at each measuring position two filter elements are to be successively inserted into the measuring light path.

Figure 10A:
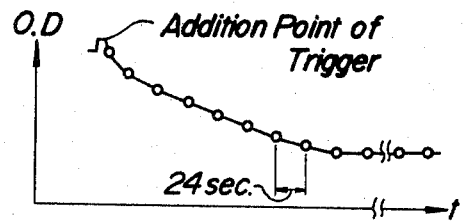
FIGS. 10A and 10B are reaction curves for explaining a manner of determining a linear reaction portion.

For each test liquid contained in the respective cuvettes, the light absorbances are measured at twenty-two measuring positions and the measuring data thus obtained is stored in a processor device, such as a computer. In this manner the variation of absorbance of the test liquid can be measured from the point in time of addition of the trigger substance at 24 second intervals as illustrated in FIG. 10A. The computer can judge from the thus stored data a linear portion of the variation curve and can derive an accurate reaction rate value on the basis of the linear portion.

Figure 10B:
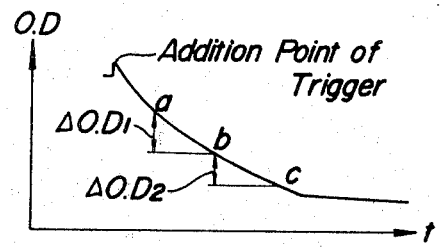

FIG. 10B shows a manner of determining the linear portion of the optical absorbance variation curve. Near the trigger addition point a given measuring point b is set as a reference point and then differences of the absorbances $\Delta OD_1$ and $\Delta OD_2$ be determined between the point b, and points a and c, respectively. Then an absolute value of these difference $|\Delta OD_1 - \Delta OD_2|$ is derived. The linear portion can be determined in such a manner that said absolute value becomes smaller or a minimum.

In order to obtain the reaction curve as shown in FIG. 10A in a precise manner, variation in outputs from the light detectors should be compensated for. To this end, prior to the measurement, a calibration cuvette having a highly accurate optical length is set in the turntable 11, and at the respective measuring point absorbances of a standard liquid such as water contained in the calibration cuvette are measured for all wavelengths $\lambda_1$–$\lambda_{10}$ and the measured absorbances are stored in the control device as calibration values. Then the absorbance values of the test liquids can be corrected by subtracting the previously stored calibration values from the measured values.

The cuvette 16 containing the test liquid for which the measurement has been completed in the above explained manner is now removed from the turntable 11 at the cuvette discharge position and the test liquid and the empty cuvette are separately discharged into the waste liquid container 6 and the waste cuvette container 5, respectively.

FIG. 11 is a cross section showing another embodiment of the measuring section taken along a diameter of a cuvette turntable 111. The turntable 111 is supported rotatably on a thermostat 118 constituting an air bath by means of a bearing 119. The thermostat 118 is formed by an inner wall 137a, an outer wall 137b and a bottom wall 137c. In a circumference of the turn table 111 is formed a gear 120 which is engaged with a gear 122 connected to a driving shaft of an electric motor 121. The motor 121 is so energized that the table 111 is rotated intermittently in the direction B at a given rate. On a rotating center axis of the turntable 111 a cylinder 124 is arranged which is connected to the outer wall 137b of the thermostat 118 by means of bridge members 123. A cover 117 is placed on the bridge members 123. In the cylinder 124 is arranged a panchromatic light source 125 aligned with the rotating center axis. Below the light source 125 are provided a heat absorbing glass plate 126 and a lens 127 which projects downwardly a parallel light flux along the rotating center axis. On the bridge 123 is secured a fan 128 for cooling the light source 125.

Below the cylinder 124 is arranged a tube-like member 130 which is rotatably supported by the thermostat 118 by means of a bearing 131. A gear 132 is formed in a periphery of a flange of the tube-like member 130. The gear 132 is engaged with a gear 134 coupled to an output shaft of an electric motor 133 which is fixed to the thermostat 118. In this manner the tube-like member 130 can be rotated by energizing the motor 133. In the tube-like member 130 is arranged a prism 136 which projects the parallel light beam from the lens 127 through a slit hole 135 formed in the tube-like member 130 onto the cuvette 16 held on the cuvette turntable 111.

In the inner wall 137a of the thermostat 118 are formed a plurality of slit holes 138, through which the measuring light beam is selectively projected onto the cuvette 16. In these slit holes 138 are secured lenses 139. In the turntable 117 is formed integrally therein light shielding flange 140 at such a position that the flange is situated between the cuvettes 16 held in the turntable 111 and the inner wall 137a. In the shielding flange 140 are formed a number of slit holes 141 corresponding to the respective cuvettes 16 for introducing the light beam into the cuvettes.

In the outer wall 137b of the thermostat 118 are arranged a number of light detectors 148 at such positions that each of them is aligned radially with the respective lens 138, holw 141 and the cuvette 16.

Coaxially with the tube-like member 130 is arranged a rotating filter holder 150 holding along its periphery a plurality of filter elements 149 having different transmitting wavelengths $\lambda_1$-$\lambda_{10}$ as shown in FIG. 12. The filter holder 150 is secured to an output shaft of an electric motor 151 fixed to the inner wall 137a of thermostat 118. Therefore, by energizing the motor 151 in a suitable manner, any desired one of filter elements 149 can be selectively inserted into the light beam between the prism 136 and the light detector 148. Output signals from the respective light detectors 148 are supplied to a processor through an analog-digital converter (not shown). There is further arranged a hot air supply device 160 which circulates the hot air stream through the thermostat 118 via a duct 162.

If the same measurement as the previous embodiment is to be effected also in this embodiment, twenty-two light detectors 142 must be provided at twenty-two cuvette stop positions and, during the one step period of the cuvette turn table 111 (i.e. six seconds), the tube-like member 130 must scan all of the twenty-two light detectors 142.

FIG. 13 is a cross section showing still another embodiment of the measuring section cut along a diameter of a cuvette turntable 211. The turntable 211 is supported rotatable on a thermostat 218 constituting an air bath by means of guide rollers 219. The thermostat 218 is formed by an inner wall 237a, an outer wall 237b and a bottom wall 237c. In a circumference of the turntable 211 is formed a gear 220 which is engaged with a gear 222 connected to a driving shaft of an electric motor 221. The motor 221 is so energized that the table 211 is rotated intermittently in the direction B at a given. At a rotating center axis of the turntable 211 is arranged a cylinder 224 which is connected to the outer wall 237c of the thermostat 218 by means of bridge members 223. A cover 217 is placed on the bridge members 223. In the cylinder 224 is arranged a cooling fan 228. Below the cylinder 224 is provided a tube-like light source (white light source) holder 270 at a lower end of which is secured a panchromatic light source 225 for projecting measuring lights toward the cuvettes 16 held in the turntable 211. In the holder 270 are formed a plurality of holes 271 between the fan 228 and the light source 225. The light source 225 is surrounded by a first cover 272 having a transparent portion through which the light is transmitted toward the cuvettes 16. In this embodiment the first cover 272 is consists of the cylindrical holder 270 and a heat resisting glass 273 having a high transmittivity. Around the cylinder 224 is arranged a shielding member 274 having a plurality of openings 272 at its top wall. The tube-like holder 270 and the first cover 272 are further surrounded by a second cover 276 having at least a transparent portion at a position opposite to the heat resisting glass 273. In the present embodiment the second cover 276 is wholly made of transparent, heat-resisting glass. According to such a construction a cooling air stream generated by the fan 228 can flow in a space between the first and second covers 272 and 276. Thus, the light source 225 is not directly exposed to the cooling air stream, so that the light output from the light source 225 can be maintained stable, while heat produced by the light source can be effectively conducted away by the cooling air stream flowing between the first and second covers 272 and 276. Further, the cooling air stream can not flow into the thermostat 218; thus the test liquids contained in the cuvettes can be maintained at the given desired reaction temperature.

In the inner wall 237a of the thermostat 218 are formed a plurality of slit holes 238 through which the measuring light beam is selectively projected onto the cuvette 16. In these slit holes 238 are secured lenses 239. In the turntable 211 is formed a light shielding flange 240. In the light shielding flange 240 are formed a number of slit holes 241 corresponding to the respective cuvettes 16 for introducing the light beam into the cuvettes.

In the outer wall 237b of the thermostat 218 are arranged a plurality of light detectors 248 at such positions that they are aligned with the slit holes 238 formed in the inner wall 237a, holes 241 formed in the shielding ring 240, and cuvettes 16 situated at the measuring positions. Between the second cover 276 and the shielding flange 240 is arranged a rotating filter holder 250 holding along at its periphery a plurality of filter elements 249 having different transmitting wavelengths $\lambda_1$-$\lambda_{10}$, just like as that shown in FIG. 12. The filter holder 250 is secured to an output shaft of an electric motor 251 fixed to the thermostat 218. Therefore, by energizing the motor 251 in a suitable manner, any desired one of filter elements 249 can be inserted into the measuring light beam between the light source 225 and the light detectors 248. Output signals from the light detectors 248 are supplied to a processor through an analog-digital converter (not shown).

The operation of the measuring section, shown in FIG. 13, is substantially identical with those of the previous embodiments. But in the present embodiment, since the light source 225 is so constructed that it can emit light over substantially 360° from the rotating center axis, it is not necessary to provide the motors 33 and 133 for rotating the prism 36 and 136, respectively. Therefore, the construction of the measuring section can be further simplified.

According to the invention since the reaction condition of the respective test liquids can be monitored on the reaction line without disturbing the stepwise transportation of the cuvettes, it is possible to obtain highly reliable and accurate analytical data. Further the panchromatic light emitted from the single light source is delivered to a number of cuvettes and the light beam transmitted trough the cuvettes are made to impinge upon one or more light detectors. Thus, the constructions of the whole apparatus and, particularly the measuring section, can be made materially simple. Therefore, the apparatus can be made much more inexpensively. Particularly in the first embodiment shown in FIG. 3, it is sufficient to provide the single light detector at the rotating center axis of the cuvette turn table; thus, the construction of the measuring section can be further simplified. Moreover since use is not made of optical fibers for guiding the light beam transmitted through the cuvette to the light detector, the light loss can be maintained small. Further, the hot air stream in the air bath could never be disturbed, the reaction temperature can be maintained uniformly.

What is claimed is:

1. An apparatus for effecting automatic analysis of test liquids contained in respective cuvettes comprising:
   a cuvette turntable for supporting a number of cuvettes along a circle, said cuvettes being rotatable about a center axis of the circle;
   means for rotating intermittently the cuvette turntable about said center axis at a given repetition rate;
   a fixed light source arranged to project a measuring light beam along the center axis;
   a rotatable first optical member rotatable about said center axis for deflecting radially with respect to the cuvette turntable the measuring light beam toward the cuvettes held in the cuvette turntable;
   a plurality of second optical members arranged at a plurality of positions outside the cuvette travelling circle for receiving the measuring light beam transmitted through the cuvettes and deflecting the light beam toward the center axis;
   a third optical member arranged at the center axis integrally with the first optical member for deflecting the measuring light beam along the center axis;
   a single light detector arranged on the center axis to receive the light beam deflected by the third optical member;
   and
   means for rotating the first and third optical members about the center axis at a higher rate than that of the cuvette turntable whereby, while the cuvette turntable is stopped, the cuvettes situated at the positions corresponding to the second optical members are successively scanned by rotating the first and third optical members.

2. An apparatus according to claim 1, wherein said first and third optical members comprise prisms supported in a rotatable tube-like member which is rotatable about the center axis.

3. An apparatus according to claim 1, further comprising an air bath type thermostat arranged beneath the cuvette turntable.

4. An apparatus according to claim 1, further comprising a filter holder comprising a plurality of filter elements which allow passage of different wavelengths and means for rotating the filter holder to insert a given desired filter element in the optical path between the third optical member and the light detector.

5. An apparatus according to claim 1, further comprising a fan for cooling the light source.

6. An apparatus according to claim 1, wherein each of said second optical elements comprises a prism.

7. An apparatus according to claim 1, wherein the cuvette turntable comprises a ring-shaped shielding flange having a number of holes for passing the measuring light beam from the first optical member to the cuvettes.

8. An apparatus according to claim 1, further comprising a tubular member arranged coaxially with the cuvette turntable and having a number of lenses for projecting the measuring light beam emitted from the light source onto the cuvettes.

9. An apparatus for effecting automatic analysis of test liquids contained in respective cuvettes comprising:
   a cuvette turntable for supporting a number of cuvettes along a circle, said cuvettes being rotatable about a center axis of the circle;
   means for rotating intermittently the cuvette turntable about said center axis at a given repetition rate;
   a fixed light source arranged to project a measuring light beam along the center axis;
   a rotatable optical member rotatable about said center axis for deflecting radially with respect to the cuvette turntable, the measuring light beam toward the cuvettes held in the cuvette turntable;
   a plurality of light detectors arranged at a plurality of positions outside the cuvette travelling circle for receiving the measuring light beam transmitted through the cuvettes; and
   means for rotating the optical member about the center axis at a higher rate than that of the cuvette turntable; whereby while the cuvette turntable is stopped, the cuvettes situated at the positions corresponding to the light detectors are successively scanned by rotating the optical member.

10. An apparatus according to claim 9, wherein said optical member comprises a prism supported in a tube-like member, said tube-like member being rotatable about the center axis.

11. An apparatus according to claim 9, further comprising an air bath type thermostat arranged beneath the cuvette turntable.

12. An apparatus according to claim 9, further comprising a filter holder comprising a plurality of filter elements which allows passage of different wavelengths and means for rotating the filter holder to insert a given desired filter element in the measuring beam path between the optical member and the cuvette.

13. An apparatus according to claim 9, further comprising a fan for cooling the light source.

14. An apparatus according to claim 9, wherein the cuvette turntable comprises a ring-shaped shielding flange having a number of holes for passing the measuring light beam from the optical member to the cuvettes.

15. An apparatus according to claim 9, further comprising a tubular member arranged coaxially with the cuvette turntable and having a number of lenses for projecting the measuring light beam emitted from the light source onto the cuvettes.

16. An apparatus for effecting automatic analysis of test liquids contained in respective cuvettes comprising:
a cuvette turntable for supporting a number of cuvettes along a circle, said cuvettes being rotatable about a center axis of the circle;
means for rotating intermittently the cuvette turntable about said center axis at a given repetition rate;
a fixed light source arranged on the center axis to sequentially project a measuring light beam toward each cuvette held in the cuvette turntable;
a plurality of light detectors arranged at a plurality of positions outside the cuvette travelling circle for receiving each measuring light beam transmitted through a cuvette;
a plurality of filter elements which allow passage of different wavelengths;
a filter holder rotatably supporting said filter elements about the center axis;
means for rotating the filter holder about the center axis to simultaneously insert a given desired filter element in each path between said light source and said light detectors; and
an optical system and plurality of slit holes fixed between the filter holder and cuvettes for converging and directing the light fluxes sequentially transmitted through the filters onto the cuvettes.

17. An apparatus according to claim 16, further comprising an air bath type thermostat arranged beneath the cuvette turntable.

18. An apparatus according to claim 16, wherein the cuvette turntable comprises a ring-shaped shielding flange having a number of holes for sequentially passing the measuring light beams from the light source to the cuvettes.

19. An apparatus according to claim 16, further comprising a first cover surrounding the light source, a second cover surrounding the first cover, and a fan which flows a cooling air stream through a space between the first and second covers.

20. An apparatus according to claim 16, further comprising a tubular member arranged coaxially with the cuvette turntable and having a number of lenses for projecting the measuring light beam emitted from the light source onto the cuvettes.

21. An apparatus for effecting automatic analysis of test liquids as in claim 16, wherein the filter holder is tubular in shape.

* * * * *